United States Patent

Heimerl et al.

[11] Patent Number: 5,147,381
[45] Date of Patent: Sep. 15, 1992

[54] SURGICAL CLIP

[75] Inventors: Albert Heimerl; Holger Kartheus, both of Hamburg, Fed. Rep. of Germany

[73] Assignee: Beiersdorf AG, Hamburg, Fed. Rep. of Germany

[21] Appl. No.: 665,365

[22] Filed: Mar. 6, 1991

[30] Foreign Application Priority Data

May 8, 1990 [DE] Fed. Rep. of Germany ....... 4014653

[51] Int. Cl.$^5$ .............................................. A61B 17/00
[52] U.S. Cl. ..................................... 606/219; 227/19; 227/902
[58] Field of Search ............. 606/219; 411/457; 227/19, 902

[56] References Cited

U.S. PATENT DOCUMENTS

| | | | |
|---|---|---|---|
| 4,261,244 | 4/1981 | Becht et al. | 606/219 |
| 4,278,091 | 7/1981 | Borgone | 606/219 |
| 4,321,001 | 3/1982 | Froehlich | 227/19 |
| 4,399,810 | 8/1983 | Samuels et al. | 227/19 |
| 4,505,273 | 3/1985 | Braun et al. | 606/219 |
| 4,583,670 | 4/1986 | Alvarado | 227/19 |
| 4,607,638 | 8/1986 | Crainich | 606/219 |
| 4,802,478 | 2/1989 | Powell | 606/219 |
| 4,887,601 | 12/1989 | Richards | 606/219 |
| 4,979,954 | 12/1990 | Gwathmeg et al. | 606/219 |

FOREIGN PATENT DOCUMENTS

| | | | |
|---|---|---|---|
| 0180820 | 5/1986 | European Pat. Off. | 227/19 |
| 2911732 | 10/1979 | Fed. Rep. of Germany | 606/219 |
| 3111996 | 10/1982 | Fed. Rep. of Germany | 606/219 |

Primary Examiner—Stephen C. Pellegrino
Assistant Examiner—Gary Jackson
Attorney, Agent, or Firm—Dvorak and Traub

[57] ABSTRACT

A surgical clip for closing the margins of a wound, is disclosed, which clip consists of a bridge and two legs having cutting edges at their ends and projecting from opposite ends of the bridge. Each leg has a part formed as an arc of a circle which adjoins the bridge, and a free ended straight section including the cutting edge of the leg, extending from the arcuate part of the leg. For reducing trama when the clip is implanted and for maintaining eversion of the wound margins after the clip has been implanted, the straight sections of the legs are set at an angle in the range of 2.5° to 10° with respect to the axis of symmetry of the clip.

9 Claims, 2 Drawing Sheets

SURGICAL CLIP

FIELD OF THE INVENTION

This invention relates to a surgical clip comprising a bridge and two legs extending therefrom on either side of an axis of symmetry of the clip, each leg having a part extending over an arc of a circle and being connected to, and projecting from, the bridge and from which arcuate part extends a straight free ended section having a cutting edge. Such clips are now commonly used for closing the margins of surgical skin wounds.

BACKGROUND OF THE INVENTION

EP-A-0 076 744, EP-A-0 284 345, U.S. Pat. No. 3 643 851 and U.S. Pat. No. 4 179 057 disclose surgical clips which are of simple U-shape, when undeformed prior to use, and are, therefore, most economical to produce. Such U-clips provide effective adaptation and eversion of the margins of a wound to be closed. A disadvantage of such clips is, however, that their cutting edges, upon seizing the margins of a wound when the clip is being implanted, tend to tear open traumatic channels in the skin and tissue, in which inflammation can occur. Also the clip tends to destroy tissue, as the clip splays apart upon its removal, so as to open regions of the wound which have already healed.

So called "D clips" which are of D-shape in their fully deformed condition are disclosed in DE-A-2 625 991, DE-A-3 204 532, U.S. Pat. No. 1 910 688 and U.S. Pat. No. 4 321 002, which yield better results insofar as the above described disadvantages are concerned. An essential feature of such a clip is that the legs of the clip are of arcuate shape with a view to ensuring that they form atraumatic puncture channels upon implantation.

It has been found, however, that "D clips" have a major disadvantage in clinical practice For good scar formations, a wound should begin to heal from the lower layer (stratum germinativum) of the epidermis, and for it to extend without bridging over malformations. Also the juxtaposition of the corium as middle skin layer and the lowermost skin layer or subcutis should, as far as possible be tension-free. To this end, the surgeon first spreads the upper skin layers at the margins of the wound to form a V-shaped parting with the point of the V in the region of the closely joined lower stratum germinativum. Since this position of the wound margins, which is known as eversion, must be maintained for some days after the closure of the wound, said position is fixed by means of a stitch. It has been found, however, that when "D clips" are used the desired eversion is not maintained, because the curved legs of the clip cannot develop sufficient retaining forces in the tissue so that the margins of the wound tend to ride up the legs of the clip. So long, however, as both margins ride up the legs of the clip to an equal extent, the resultant effect, although not desired, is normally tolerable in so far as the healing of the wound is concerned and shows up as a relatively wide scar formation.

If, however, the margins of the wound are displaced in opposite directions, or to different extents, on the legs of the clip, the margins of the wound will form a step as they heal, so that the resulting scars will be conspicuous. Since the three upper skin layers will be out of alignment with each other, the organism will itself even out the skin layers so that a relatively wide scar is produced.

In the light of the foregoing it may be said that "U-clips" cannot be implanted or removed without trauma, but are otherwise capable of maintaining eversion of the margins of the wound and that although "D clips" can in general be used without trauma, they fail to provide lasting eversion of the margins of the wound.

Both "U clips" and "D clips" have the further disadvantage that are not compatible with variations of the margins of a wound. Especially in the case of orthopedic operations, for example the implanting of artificial hip joints, the margins of the wound are subjected to severe mechanical stress by the instrumentation and, therefore, become more swollen than the margins of normal skin incisions. By reason of such swelling the legs of an implanted clip are forced apart by the pressure of the tissue so that the clip, and thus the wound, are partially reopened.

SUMMARY OF THE INVENTION

The present invention is intended to provide a surgical clip which is compatible with variations in the margins of a wound, and which will have sufficient retaining force when it is not in a fully deformed, that is to say a fully closed, condition, such adaption finding application not only in the case of substantial swelling of the wound tissues, but also where it is important to avoid unnecessary injury to the subcutis, in the fixing of skin grafts, for example. The invention is also intended to provide a surgical clip which is economical to produce and which enables largely atraumatic union of the margins of a wound, while affording lasting eversion. According to the present invention the straight sections of the legs of a surgical clip of the kind to which the present invention relates, are set at an angle $\alpha$ of $2.5° \leq \alpha \leq 10°$, with respect to the axis of symmetry of the surgical clip.

The dimension of the angle $\alpha$ has a direct influence upon the width of the puncture channels made by the legs of the clip since the arcuate parts of the legs follow the straight sections thereof as the clip is being implanted, so that in principle only atraumatic channels of a diameter corresponding to that of the cross section of the clip are produced.

The greater is the angle $\alpha$, the larger is the width of the puncture channels, these being, in part, traumatically formed. Nevertheless, as the angle $\alpha$ is increased, the more firmly are the legs of the clip anchored in the tissue and the margins of the wound more effectively restrained from riding up the legs of the clip. The possibility of variable adaption of the wound margins that is to say by joining them by means of clips which are only partially deformed is relatively unaffected by the magnitude of the angle $\alpha$.

A CAD study with a view to determining how puncture channels of the smallest possible size can be obtained, has shown that the angle $\alpha$ should lie in the range of 2.5° to 10° and for particularly favourable results, in the range of 7° to 7.5°.

Where the clip is to be universally suitable for a wide range of use, covering the field of plastic surgery, the angle $\alpha$ will generally be smaller, being of the order of 4° to 6°, and preferably being 5°.

In any event the use of such values of the angle $\alpha$, which may vary in absolute magnitude by ±15%, yields puncture channels of small width and to a large extent avoids traumatic puncturing, whilst affording trouble free fixing of the wound margins and sustained eversion thereof.

The bridge of the clip may be straight there being smooth transitions between the bridge and the arcuate parts of the legs. There may also be smooth transitions between the arcuate parts and the straight sections of the legs and kinks may be formed in the legs, at these transitions. The angle $\beta$ through which the arcuate parts of the legs extend may be $80° \leq \beta \leq 100°$, the angle $\beta$ being measured between, an imaginary perpendicular extending through the radius point of the arc of the arcuate part of the leg and the bridge of the clip; and the point of transition between the arcuate part of the leg and the straight section thereof.

DETAILED DESCRIPTION OF THE INVENTION

Figure 1:
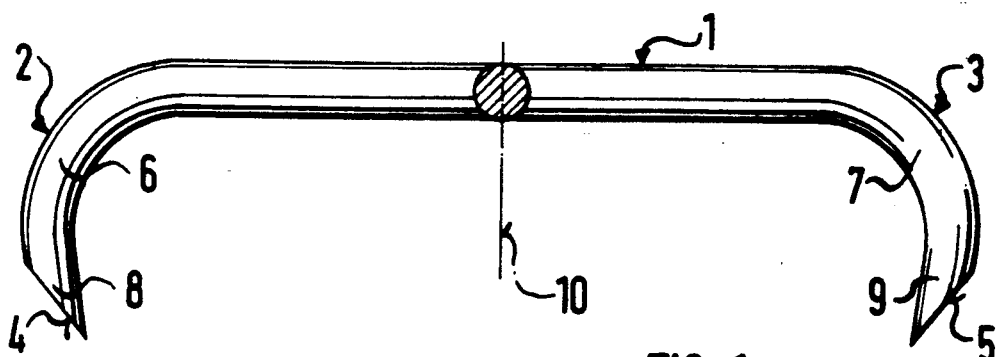
FIG. 1 is an elevation of a surgical clip according to an embodiment of the invention.
Figure 2:
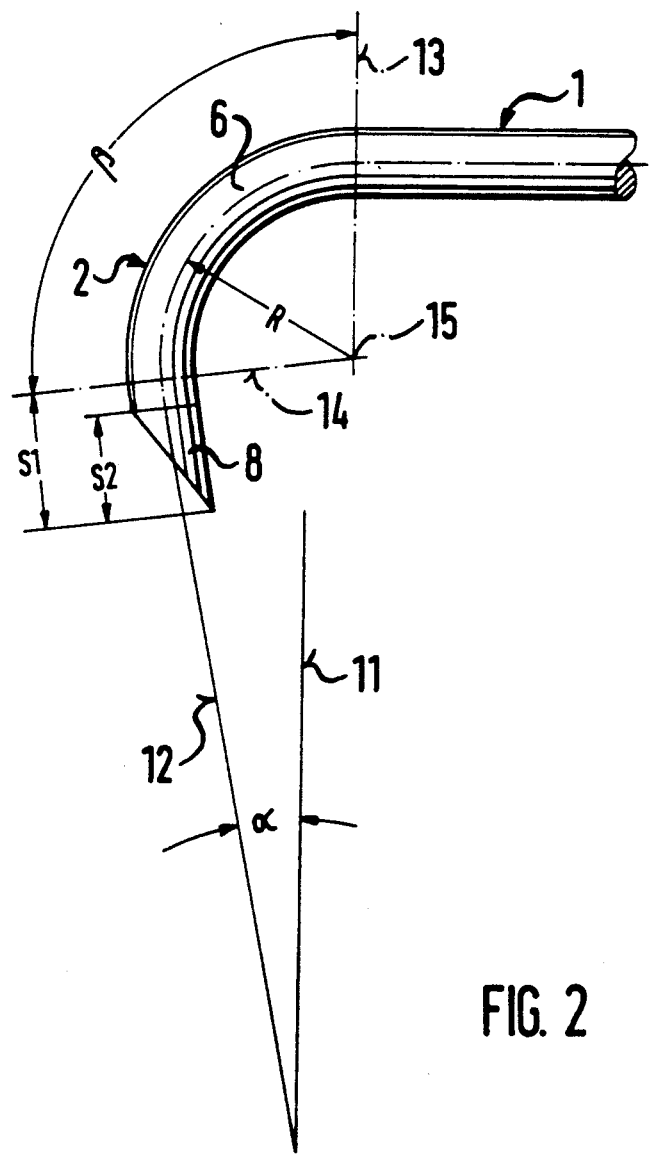
FIG. 2 is an enlarged fragmentary view of a detail of FIG. 1.

As shown in FIG. 1 a surgical clip in particular for drawing together margins of a wound, consists of a straight bridge 1, and legs 2 and 3 each connected to, and projecting from, a respective end of the bridge 1, the legs 2 and 3 terminating in respective cutting edges 4 and 5 remote from the bridge 1, for seizing the margins of the wound. The legs 2 and 3 have respective arcuate parts 6 and 7, each of which extends from the bridge 1 over an angle $\beta$ through an arc of a circle having a radius R (FIG. 2). The legs 2 and 3 have straight sections 8 and 9 respectively, extending from ends of the arcuate parts 6 and 7, respectively, remote from the bridge 1 and including the cutting edges 4 and 5, respectively. Each straight section extends over a length S1 (FIG. 2).

The arcuate parts 6 and 7 have transitions merging smoothly with the bridge 1 and with the straight sections 8 and 9. The sections 8 and 9 are set at an angle $\alpha$ with respect to the plane of symmetry 10 of the clip and/or with respect to a plane 11 parallel therewith. An imaginary extension 12 of the central axis of each section 8 and 9 intersects said planes at the angle $\alpha$ which has the order of magnitude $2.5 \leq \alpha \leq 10°$. Thus the angle $\alpha$ lies in the range 2.5° to 10°. Narrower ranges of the angle $\alpha$ are suitable for particular applications as set forth in the foregoing, for example the range 7° to 7.5°.

Each angle $\beta$ is defined by an imaginary perpendicular 13 and an imaginary straight line 14 extending through the transitions between the arcuate part 6 and the straight section 8 of the leg 2, and between the arcuate part 7 and the straight section 9 of the leg 3. The imaginary perpendicular 13 intersects the radius point 15 and intersects the bridge 1 at right angles thereto.

Each perpendicular 13 intersects the clip at the point of transition between the arcuate part 6 or 7, as the case may be, of the respective leg 2 or 3, and the bridge 1, provided that such transition is smooth.

Figure 5:
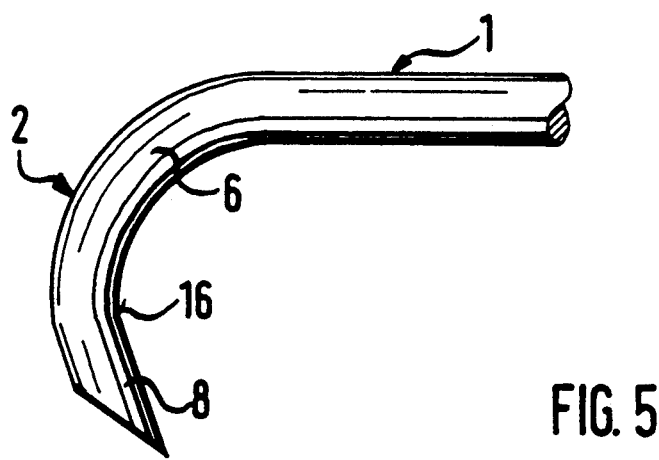
FIG. 5 is a similar view to that of FIG. 2, but illustrating a modification of the clip.

The order of magnitude of each angle $\beta$ should lie within the range $80° \leq \beta \leq 100°$ although the magnitude of the angle $\beta$ to some extent depends upon that chosen for the angles $\alpha$. The angles $\alpha$ and $\beta$ may be adapted and matched by forming a kink 16 (FIG. 5) at the transition between the arcuate part of each leg 2 and 3 and the straight section thereof. This expedient is applicable in particular in respect of angles $\beta$ of below 90° or which only slightly exceed that value. The angle $\alpha$ can in each case be obtained by selecting the extent of the kinks 16.

As shown, the straight sections 8 and 9 each of which extends over the length S1, each includes the respective angled cutting edge 4 or 5 and a portion having the full cross sectional area of the clip. Nevertheless, each straight section 8 and 9 may be shorter so as to extend over a length S2 (FIG. 2) corresponding to the length of the respective cutting edge 4 or 5.

Figure 3:
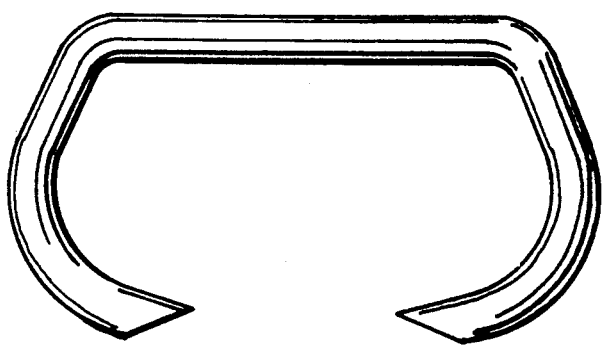
FIG. 3 is an elevation of the clip showing it in a partially closed condition.

Instruments for implanting surgical clips are generally known and so will not be described here. With such an instrument which is of appropriate design the clip may intentionally be deformed into a partially closed condition as shown in FIG. 3, for use, for example, for the variable adaption of the margins of wounds or for the fixing of skin grafts.

Figure 4:
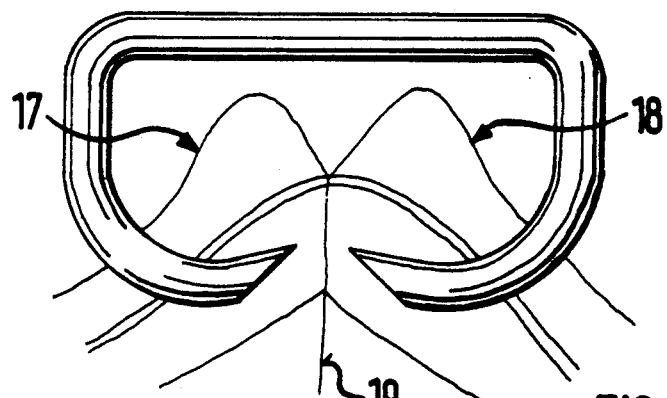
FIG. 4 is an elevational view showing the clip in a fully closed position when implanted in the margins of a wound.

FIG. 4 shows the clip in a fully closed and implanted condition. As will clearly be apparent from FIG. 4, the wound margins 17 and 18 (shown schematically) are everted, the straight sections of the clip supporting the overlying tissue and thereby sustaining the eversion of said margins, without the possibility of the tissue riding up the legs so that the eversion disappears, as could occur should the legs be wholly formed as arcs.

What is claimed is:

1. A surgical clip having an axis of symmetry and comprising a bridge and two legs extending therefrom, one on each side of said axis of symmetry, each leg having a part extending over an arc of a circle and being connected to, and projecting from, the bridge, from which arcuate part extends a straight free ended section having a cutting edge, wherein each straight section is set at an angle which lies in the range of 2.5° to 10° with respect to said axis of symmetry.

2. A surgical clip as claimed in claim 1, wherein said angle lies in the range of 7° to 7.5° with respect to said axis of symmetry.

3. A surgical clip as claimed in claim 1, wherein said angle lies in the range of 4° to 6° with respect to said axis of symmetry.

4. A surgical clip as claimed in claim 1, wherein said angle is of 5° with respect to said axis of symmetry.

5. A surgical clip as claimed in claim 1, wherein the bridge is straight.

6. A surgical clip as claimed in claim 1, comprising smooth transitions between the arcuate parts of the legs and the bridge.

7. A surgical clip as claimed in claim 1, comprising smooth transitions between the arcuate parts of the legs and the straight free ended sections thereof.

8. A surgical clip as claimed in claim 1, wherein the legs are formed with kinks at transitions between the arcuate parts and said straight sections of the legs.

9. A surgical clip as claimed in claim 1, wherein the angle over which the arcuate part of each leg extends, as measured between an imaginary perpendicular intersecting the radius point of the arc of such arcuate part and intersecting the bridge, and the junction between such arcuate part and the straight section of said leg lies in the range of 80° to 100°.

* * * * *